(12) United States Patent
Wohabrebbi et al.

(10) Patent No.: US 8,956,636 B2
(45) Date of Patent: Feb. 17, 2015

(54) METHODS AND COMPOSITIONS FOR TREATING POSTOPERATIVE PAIN COMPROSING KETOROLAC

(75) Inventors: Amira Wohabrebbi, Memphis, TN (US); William F. McKay, Memphis, TN (US); Christopher M. Hobot, Tonka Bay, MN (US); Keith R. Hildebrand, Houlton, TN (US); Edward Phillip McDonald, Plymouth, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1219 days.

(21) Appl. No.: 12/388,635

(22) Filed: Feb. 19, 2009

(65) Prior Publication Data

US 2009/0263319 A1 Oct. 22, 2009

Related U.S. Application Data

(60) Provisional application No. 61/046,269, filed on Apr. 18, 2008.

(51) Int. Cl.
| | | |
|---|---|---|
| A61F 13/00 | (2006.01) | |
| A61K 9/14 | (2006.01) | |
| A61K 31/407 | (2006.01) | |
| A61K 9/00 | (2006.01) | |
| A61K 9/16 | (2006.01) | |
| A61K 49/04 | (2006.01) | |

(52) U.S. Cl.
CPC .............. *A61K 31/407* (2013.01); *A61K 9/0024* (2013.01); *A61K 9/1647* (2013.01); *A61K 49/0404* (2013.01); *A61K 49/0419* (2013.01)
USPC .......................................... 424/422; 424/484

(58) Field of Classification Search
None
See application file for complete search history.

(56) References Cited

U.S. PATENT DOCUMENTS

| | | | |
|---|---|---|---|
| 4,624,255 | A | 11/1986 | Schenck et al. |
| 4,863,457 | A | 9/1989 | Lee |
| 5,522,844 | A | 6/1996 | Johnson |
| 5,626,838 | A | 5/1997 | Cavanaugh, Jr. |
| 5,868,789 | A | 2/1999 | Huebner |
| 6,069,129 | A | 5/2000 | Sandberg et al. |
| 6,179,862 | B1 | 1/2001 | Sawhney |
| 6,287,588 | B1 | 9/2001 | Shih et al. |
| 6,331,311 | B1 | 12/2001 | Brodbeck et al. |
| 6,428,804 | B1 | 8/2002 | Suzuki et al. |
| 6,461,631 | B1 | 10/2002 | Dunn et al. |
| 6,589,549 | B2 | 7/2003 | Shih et al. |
| 6,630,155 | B1 | 10/2003 | Chandrashekar et al. |
| 6,632,457 | B1 | 10/2003 | Sawhney |
| 6,756,058 | B2 | 6/2004 | Brubaker et al. |
| 6,773,714 | B2 | 8/2004 | Dunn et al. |
| 6,974,462 | B2 | 12/2005 | Sater |
| 7,144,412 | B2 | 12/2006 | Wolf et al. |
| 7,166,570 | B2 | 1/2007 | Hunter |
| 7,220,281 | B2 | 5/2007 | Lambrecht et al. |
| 7,229,441 | B2 | 6/2007 | Trieu et al. |
| 7,235,043 | B2 | 6/2007 | Gellman et al. |
| 7,318,840 | B2 | 1/2008 | McKay |
| 7,329,259 | B2 | 2/2008 | Cragg |
| 7,361,168 | B2 | 4/2008 | Makower et al. |
| 7,367,978 | B2 | 5/2008 | Drewry et al. |
| 2002/0009454 | A1 | 1/2002 | Boone et al. |
| 2002/0090398 | A1 | 7/2002 | Dunn et al. |
| 2003/0204191 | A1 | 10/2003 | Sater et al. |
| 2003/0224033 | A1 * | 12/2003 | Li et al. .......................... 424/423 |
| 2004/0072799 | A1 | 4/2004 | Li et al. |
| 2004/0082540 | A1 | 4/2004 | Hermida Ochoa |
| 2004/0214793 | A1 | 10/2004 | Hermida Ochoa |
| 2005/0142163 | A1 | 6/2005 | Hunter et al. |
| 2005/0186261 | A1 | 8/2005 | Avelar et al. |
| 2005/0197293 | A1 | 9/2005 | Mellis et al. |
| 2006/0106361 | A1 | 5/2006 | Muni et al. |
| 2006/0148903 | A1 | 7/2006 | Burch et al. |
| 2006/0183786 | A1 | 8/2006 | Wang |
| 2006/0189944 | A1 | 8/2006 | Campbell et al. |
| 2007/0156180 | A1 | 7/2007 | Jaax et al. |
| 2007/0185497 | A1 | 8/2007 | Cauthen et al. |
| 2007/0202074 | A1 | 8/2007 | Shalaby |
| 2007/0243225 | A1 | 10/2007 | McKay |
| 2007/0243228 | A1 | 10/2007 | McKay |
| 2007/0248639 | A1 | 10/2007 | Demopulos et al. |
| 2008/0091207 | A1 | 4/2008 | Truckai et al. |

FOREIGN PATENT DOCUMENTS

WO    WO 2004/080436    *    9/2004    ............... A61K 9/00

OTHER PUBLICATIONS

Moniche et al., in Anesthesiology 2002, 96, 725-741.*
Al Malyan et al. in the Journal of Craniofacial Surgery (17,(2) 302-313, 2006).*
NIH Medline' (www.nlm.nih.gov/ medlineplus/druginfo/meds/a693001.html).*
Ranjan Sinha et al. in Drug Delivery 12:133-139, 2005.*
LeRoux et al. in Acta Neurochirurgica (1999) 141: 261-267.*
Kim et al. (International Journal of Pharmaceutics, 2005, 304, 165-177).*

* cited by examiner

*Primary Examiner* — Dennis Heyer
*Assistant Examiner* — Daniel M Podgorski
(74) *Attorney, Agent, or Firm* — Sorell Lenna & Schmidt LLP

(57) ABSTRACT

Methods and compositions are provided for reducing, treating or preventing postoperative pain or inflammation in a patient in need of such treatment, the methods and compositions comprising administering one or more biodegradable drug depots comprising a therapeutically effective amount of ketorolac or pharmaceutically acceptable salt thereof to a target tissue site, wherein the drug depot releases an effective amount of ketorolac or pharmaceutically acceptable salt thereof over a period of 3 to 10 days.

15 Claims, 5 Drawing Sheets

METHODS AND COMPOSITIONS FOR TREATING POSTOPERATIVE PAIN COMPROSING KETOROLAC

This application claims the benefit of the filing date of Provisional Application No. 61/046,269 filed Apr. 18, 2008, entitled "Methods And Compositions For Treating Postoperative Pain Comprising Ketorolac" this entire disclosure is hereby incorporated by reference into the present disclosure.

BACKGROUND

Pain relief is of prime importance to anyone treating patients undergoing surgery. Proper pain relief imparts significant physiological and psychological benefits to the patient. Not only does effective pain relief mean a smoother more pleasant postoperative course (e.g., mood, sleep, quality of life, etc.) with earlier discharge from medical/surgical/outpatient facilities, but it may also reduce the onset of chronic pain syndromes (e.g., fibromyalgia, myalgia, etc.).

Pain serves a biological function. It often signals the presence of damage or disease within the body and is often accompanied by inflammation (redness, swelling, and/or burning). In the case of postoperative pain it may be a result of the surgery, or other treatments such as, for example, management of acute pain following burns or non-surgical trauma. The goal for postoperative pain management is to reduce or eliminate pain and discomfort with medication that cause minimum or no side effects.

The site of the surgery has a profound effect upon the degree of postoperative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to postoperative ileus, nausea, vomiting and urinary retention. These problems are unpleasant for the patient and may prolong hospital stay. Most patients who experience moderate to severe post-operative pain, post-traumatic pain and burn pain, often require pain control at least in the first 3 days after trauma or surgery.

Ketorolac is a non-steroidal anti-inflammatory drug (NSAID) with not only anti-inflammatory properties, but also analgesic properties similar to opioids although it is not a narcotic. Ketorolac as an NSAID also has antipyretic activities to reduce elevated body temperature.

In general the chemical name of ketorolac is (+/−)-5-benzoyl-2,3-dihydro-1H-pyrrolizine-1-carboxylic acid or 5-benzoyl-1,2-dihydro-3H-pyrrolo[1,2-a]pyrrole-1-carboxylic acid. Ketorolac has a molecular weight of 255.27 and exhibits the following general structure:

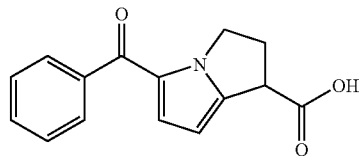 [SMILES: O=C(c1ccccc1)c1ccc2n1CCC2C(=O)O]

The major mechanism by which ketorolac exerts its pharmacological effects is by the inhibition of prostaglandin synthesis. In particular, it is believed that the primary action of ketorolac (as all NSAIDs) is to inhibit cyclooxygenase, which is responsible for the biosynthesis of prostaglandins, prostacyclin and thromboxane. Prostaglandins, which are released from virtually all tissues in response to direct trauma or surgery, act to mediate pain and inflammation.

Preoperative administration of ketorolac reduces pain in the immediate post-operative period. Combination therapy with ketorolac and opioids results in a significant 25% to 50% reduction in morphine and fentanyl requirements in the first 1 to 2 post-operative days, and may be accompanied by a reduction in opioid-induced adverse events. In addition, when using ketorolac, some patients experience a more rapid return to normal gastrointestinal function and shorter stay in hospitals as opioids tend to slow bowel function and cause constipation.

Ketorolac's analgesic efficacy in the postoperative setting has been evaluated in patients exhibiting various stages of pain in both hospital inpatients and outpatients. Intramuscular administration of doses of 10-30 mg ketorolac can provide an analgesic efficacy similar to that of intramuscular administration of 6-12 mg of the opioid morphine.

Currently, ketorolac is commercially available for intramuscular (IM), intravenous (IV), subcutaneous (SC) or oral administration, and is indicated for the short-term treatment of moderate to severe pain. The usual parenteral dosage of ketorolac is 10-30 mg every 4 to 6 hours IV or IM with a maximum total daily dose of 90 mg and a maximum duration of therapy of 5 days. For post-operative analgesia, single or multiple doses of intramuscular or intravenous administration of 10-30 mg ketorolac can provide an analgesic efficacy similar 6-12 mg morphine IM or 2-4 mg morphine IV.

Ketorolac has been administered IV for patient-controlled analgesia at a dose of 5 mg/h to provide pain relief similar to that of a morphine dose of 1 mg/h in patients after major abdominal surgery. SC administration of 60-120 mg/day of ketorolac may be beneficial in the treatment of some patients with cancer pain, especially those with a component of pain resulting from bone metastases, and may be accompanied by a concomitant reduction in opioid dosage.

Unfortunately, currently available ketorolac formulations, although effective for treating postoperative pain, require frequent single dose administration every 4 to 12 hours on an as needed basis. Often with the single dose ketorolac dosing, the patient will experience break through pain and anxious "clock-watching" waiting for the next dose in order to provide persistent pain release. These single dose ketorolac formulations are inconvenient and may interfere with the patient's postoperative inpatient and/or outpatient daytime activities and nighttime sleep and recovery.

New ketorolac compositions and methods are needed to prevent, treat or reduce postoperative pain or inflammation. Ketorolac compositions and methods that reliably provide long acting analgesic and anti-inflammatory effects over periods of 3 to 10 days are needed.

SUMMARY

New ketorolac compositions and methods are provided that effectively prevent, treat or reduce postoperative pain or inflammation. In various embodiments, ketorolac compositions and methods are provided that have long acting analgesic and anti-inflammatory effects over periods of 3 to 10 days in a single drug depot or multiple drug depots. New ketorolac compositions and methods are provided, which can easily allow accurate and precise implantation of a drug depot containing ketorolac with minimal physical and psychological trauma to a patient. One advantage of the ketorolac drug depot compositions and methods is that the drug depot can now be easily delivered to the target tissue site (e.g., spine, knee, shoulder, hip, abdomen, synovial joint, at or near the spinal column, surgical wound or incision, etc.) and provide pain relief for 3 to 10 days. In this way, accurate and precise implantation of the drug depot in a minimally invasive procedure can be accomplished.

In one exemplary embodiment, a method of treating or preventing postoperative pain or inflammation in a patient in need of such treatment is provided, the method comprising administering one or more biodegradable drug depots comprising a therapeutically effective amount of ketorolac or pharmaceutically acceptable salt thereof to a target tissue site beneath the skin (e.g., surgical wound site), wherein the drug depot releases an effective amount of ketorolac or pharmaceutically acceptable salt thereof over a period of 3 to 10 days.

In another exemplary embodiment, a method of inhibiting postoperative pain or inflammation in a patient in need of such treatment is provided, the method comprising delivering one or more biodegradable drug depots comprising a therapeutically effective amount of ketorolac or pharmaceutically acceptable salt thereof to a target tissue site beneath the skin before, during or after surgery, wherein the drug depot releases an effective amount of ketorolac or pharmaceutically acceptable salt thereof over a period of 3 to 10 days.

In yet another exemplary embodiment, an implantable or injectable drug depot useful for preventing or treating postoperative pain or inflammation in a patient in need of such treatment is provided, the implantable drug depot comprising a therapeutically effective amount of ketorolac or pharmaceutically acceptable salt thereof, the depot being implantable at a surgical wound site beneath the skin to prevent, treat or inhibit postoperative pain, wherein the drug depot is capable of releasing an effective amount of ketorolac or pharmaceutically acceptable salt thereof over a period of 3 to 10 days.

In still yet another exemplary embodiment, a method of making an implantable or injectable drug depot is provided, the method comprising combining a biocompatible polymer and a therapeutically effective amount of ketorolac or pharmaceutically acceptable salt thereof and forming the implantable drug depot from the combination Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
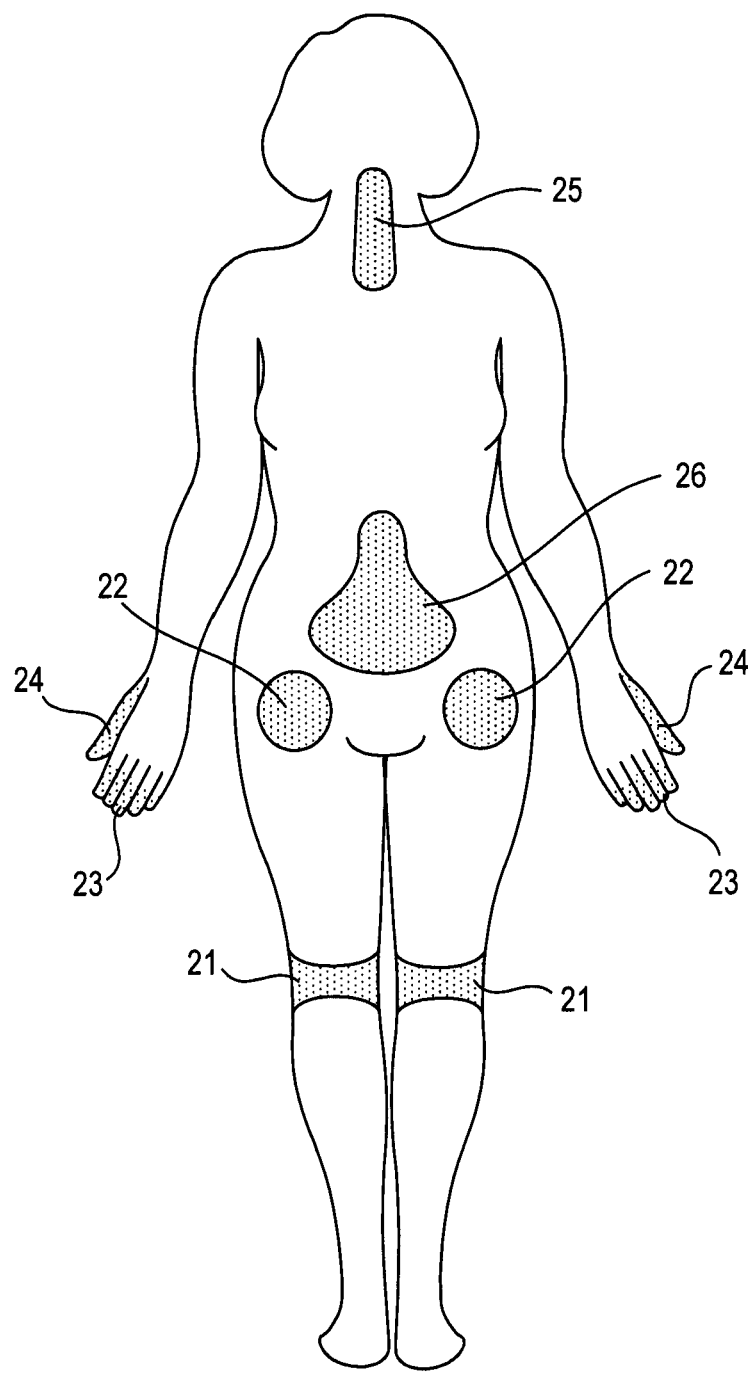
FIG. 1 illustrates a number of common locations within a patient that may be sites where surgery is conducted and locations where the drug depot containing ketorolac can locally be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New ketorolac compositions and methods are provided that effectively prevent, treat or reduce postoperative pain or inflammation. In various embodiments, ketorolac compositions and methods are provided that have long acting analgesic and anti-inflammatory effects over periods of 3 to 10 days in a single drug depot or multiple drug depots. New ketorolac compositions and methods are provided, which can easily allow accurate and precise implantation of a drug depot containing ketorolac at the surgical wound site with minimal physical and psychological trauma to a patient following various surgical procedures. One advantage of the ketorolac drug depot compositions and methods is that the drug depot can now be easily delivered to the target surgical tissue site (e.g., abdomen, synovial joint, at or near the spinal column, etc.). In this way, accurate and precise implantation of the drug depot in a minimally invasive procedure can be accomplished. By delivering an analgesic drug depot at the surgical wound site before wound closure, post-operative pain control is achieved over the period of 3 to 10 days post-surgery In one embodiment, a method of treating, preventing or reducing postoperative pain or inflammation in a patient in need of such treatment is provided, the method comprising administering one or more biodegradable drug depots comprising a therapeutically effective amount of ketorolac or pharmaceutically acceptable salt thereof to a target surgical tissue site beneath the skin, wherein the drug depot releases an effective amount of ketorolac or pharmaceutically acceptable salt thereof over a period of 3 to 10 days.

Ketorolac

The ketorolac is the active ingredient contained in a drug depot. A drug depot comprises a physical structure to facilitate implantation and retention in a desired site (e.g., a synovial joint, a disc space, a spinal canal, abdominal area, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "analgesic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent for delivery to the site. In various embodiments, the drug depot provides an optimal drug concentration gradient of the therapeutic agent at a distance of up to about 1 cm to about 5 cm from the implant site.

A "therapeutically effective amount" or "effective amount" is such that when administered, the drug results in alteration of the biological activity, such as, for example, inhibition of inflammation, reduction or alleviation of pain, improvement in the condition, etc. In various embodiments, the therapeutically effective amount of ketorolac comprises from about 5mg, 10mg, 15mg, 20mg, 25mg, 30mg, 35mg, 40mg, 45mg, 50mg, 55mg, 60mg, 65mg, 70mg, 75mg, 75mg, 80mg, 85mg, 90mg, 95mg, 100mg, 105mg, 110mg, 115mg, 120mg, 125mg, 130mg, 135mg, or 140mg of ketorolac per day. It will be understood that the dosage administered to a patient can be as single depot or multiple depots depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. For example, lower daily doses of ketorolac may be needed when there is concurrent treatment with an opioid (e.g., morphine), alternatively, the patient may require higher doses of ketorolac as the dosage of the opioid (e.g., morphine) is reduced or eliminated to control postoperative pain.

In various embodiments a therapeutically effective amount of ketorolac is provided to inhibit, treat and/or prevent postoperative pain or inflammation. In general the chemical name of ketorolac is (+/−)-5-benzoyl-2,3-dihydro-1H-pyrrolizine-1-carboxylic acid or 5-benzoyl-1,2-dihydro-3H-pyrrolo[1,2-a]pyrrole-1-carboxylic acid. Ketorolac has a molecular weight of 255.27 and exhibits the following general structure:

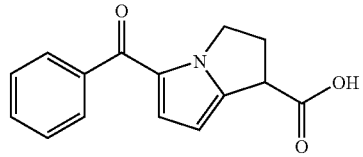 [SMILES: O=C(c1ccccc1)c1ccc2n1CCC2C(=O)O]

Ketorolac is described in U.S. Pat. No. 4,089,969, the entire disclosure is herein incorporated by reference. Ketorolac includes, but is not limited to, (+/−)-5-benzoyl-2,3-dihydro-1H-pyrrolizine-1-carboxylic acid or 5-benzoyl-1,2-dihydro-3H-pyrrolo[1,2-a]pyrrole-1-carboxylic acid or the pharmaceutically acceptable non-toxic esters or salts thereof, as disclosed in U.S. Pat. No. 4,089,969. Ketorolac includes the racemic mixtures ((+)-R and (−)-S enantiomers) or each of the dextro and levo isomers of ketorolac individually. Ketorolac includes the free acid as well as the tromethamine salt or any other pharmaceutically acceptable salt of any one of the foregoing. The ketorolac may also be pegylated for long acting activity.

Pharmaceutically acceptable esters of ketorolac include but are not limited to, alkyl esters derived from hydrocarbons of branched or straight chain having one to about 12 carbon atoms. Examples of such esters are methyl, ethyl, propyl, isopropyl, butyl, t-butyl, isoamyl, pentyl, isopentyl, hexyl, octyl, nonyl, isodecyl, 6-methyldecyl or dodecyl esters.

Pharmaceutically acceptable salts of ketorolac include salts derived from either inorganic or organic bases. Salts derived from inorganic bases include, but are not limited to, sodium, potassium, lithium, ammonium, calcium, magnesium, ferrous, zinc, copper, manganese, aluminum, ferric, manganic salts or the like. Salts derived from pharmaceutically acceptable organic non-toxic bases include, but are not limited to, salts of primary, secondary, or tertiary amines, substituted amines including naturally occurring substituted amines or cyclic amines or basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins or the like.

In various embodiments, the ketorolac comprises mixture of (+)R and (−)-S enantiomer of ketorolac. In various embodiments, the ketorolac comprises tromethamine salt of ketorolac or trometamol in a 1:1 racemic mixture that is available from various manufacturers including Roche Pharmaceuticals.

In addition to ketorolac, the drug depot may comprise one or more additional therapeutic agents. Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (ST1571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

In addition to the ketorolac, the depot may contain other therapeutic agents including alpha receptor agonists (e.g., alpha-1 or alpha-2 receptor agonist or combinations thereof). Examples of alpha-1 adrenergic receptor agonists include, but are in no way limited to methoxamine, methylnorepinephrine, norepinephrine, metaminol, oxymetazoline, phenylephrine, 2-(anilinomethyl)imidazolines, synephrine, or a combination thereof.

In some embodiments, the alpha adrenergic receptor agonist comprises an alpha-2 adrenergic receptor agonist, which acts as an analgesic and/or anti-inflammatory agent. Examples of alpha-2 adrenergic receptor agonists useful in the present application include, but are in no way limited to L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, moxonidine, mivazerol, rilmenidine, UK 14,304, B-HT 933, B-HT 920, octopamine or a combination thereof.

Other alpha adrenergic agonists include, but are not limited to, amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

The depot comprises the therapeutic agent or agents and may also contain other non-active ingredients. It has a multifunctional purpose including the carrying, stabilizing and controlling the release of the therapeutic agent(s). The controlled release process, for example, may be by a solution-diffusion mechanism or it may be governed by an erosion-controlled process. Typically, the depot will be a solid, semi-solid or formulation comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements. The formulation can be injected at or near a target tissue site beneath the skin.

In various embodiments, the depot material will be durable within the tissue site for a period of time equal to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded therapeutic agent(s).

In various embodiments, the drug depot may be designed to release the ketorolac when certain trigger points are reached (e.g., temperature, pH, etc.) after implantation or injection in vivo. For example, the drug depot may comprise polymers that will release more drug as the body temperature reaches greater than, for example, 102° F., particularly if the drug possesses antipyretic properties such as ketorolac. In various embodiments, depending on the site of implantation, the drug depot may release more or less drug as a certain pH is reached. For example, the drug depot may be designed to release the drug as the bodily fluid having a certain pH contact the drug depot (e.g., CSF having a pH of about 7.35 to about 7.70, synovial fluid having a pH of about 7.29 to about 7.45; urine having a pH of about 4.6 to about 8.0, pleural fluids having a pH of about 7.2 to about 7.4, blood having a pH of about 7.35 to about 7.45, etc.)

In various embodiments, the depot may have a high drug loading, such that the ketorolac and/or other therapeutic agent comprises about 5-99 wt % of the depot, or 30-95 wt % of the depot, or 50-95 wt % of the depot. In various embodiments, the amount of ketorolac and/or other therapeutic agent are present in the depot in a range from about 0.1% to about 40% by weight of the depot (including 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.1-10%, 10-20% and 20-30%, etc.). In various embodiments, ketorolac tromethamine can be used in a load range of 2-20%.

In various embodiments, the drug depot may release 5mg, 10mg, 15mg, 20mg, 25mg, 30mg, 35mg, 40mg, 45mg, 50mg, 55mg, 60mg, 65mg, 70mg, 75mg, 75mg, 80mg, 85mg, 90mg, 95mg, 100mg, 105mg, 110mg, 115mg, 120mg, 125mg, 130mg, 135mg, or 140mg of ketorolac per day for a total of 3 to 10 days, or 3 to 5 days. In various embodiments, the drug depot may release 0.1 mg to 6 mg of ketorolac per hour for a total of 3 to 10 days, or 3 to 5 days to reduce, treat or prevent postoperative pain. In various embodiments, the drug depot releases 5%, 10%, 15%, 20%, 25%, 30%, 40%, 50%, 60%, 70%, 80%, 90%, 95%, or 99% of the ketorolac over a period of 3 to 10 days after the drug depot is administered to the target tissue site or 5 to 7 days. The drug depot may have a "release rate profile" that refers to the percentage of active ingredient that is released over fixed units of time, e.g., mg/hr, mg/day, 10% per day for ten days, etc. As persons of ordinary skill know a release rate profile may be but need not be linear. In various embodiments, the drug depot comprises from about 2.5% to 60% by weight ketorolac, from about 20% to 95% by weight PLGA, 5% to 30% by weight of mPEG. The ester form of ketorolac being more hydrophobic may, in various embodiments, provide a better release profile.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes but is not limited to capsules, microspheres, microparticles, microcapsules, microfibers particles, nanospheres, nanoparticles, coating, matrices, wafers, pills, pellets, ribbons, strips, fibers, microfiber, meshfiber, emulsions, liposomes, micelles, gels, or other pharmaceutical delivery compositions. The drug depot may comprise a pump that holds and administers the pharmaceutical. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that depot (e.g., microparticle, microsphere, gel, etc.) can break down or degrade within the body to non-toxic components after or while a therapeutic agent has been or is being released. By "bioerodible" it is meant that the depot and/or gel will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a bioabsorbable, a bioabsorbable, and/or a biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG), PEG 200, PEG 300, PEG 400, PEG 500, PEG 550, PEG 600, PEG 700, PEG 800, PEG 900, PEG 1000, PEG 1450, PEG 3350, PEG 4500, PEG 8000, conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, POE, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the drug depot comprises poly (lactide-co-glycolide) (PLGA), polylactide (PLA), polyglycolide (PGA), D-lactide, D,L-lactide, L-lactide, D,L-lactide-ϵ-caprolactone, D,L-lactide-glycolide-ϵ-caprolactone or a combination thereof.

In various embodiments, when the drug depot comprises a polymer, it is employed at about 10 wt % to about 90 wt % or about 30 wt % to about 60 wt % based on the weight of the drug depot.

As persons of ordinary skill in the art are aware, an implantable depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

In some embodiments, at least 75% of the particles have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to about 50,000.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area or joint area, in various embodiments, the depot may comprise sterile preservative free material.

Some examples of excipients that may be in the depot include, for example, mPEG, sorbitol, D-sorbitol, maltodextrin, cyclodextrin, B-cyclodextrin, POE or combinations thereof. The excipients may be added in weight percentages from 0.5% to 20%.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film, ribbon or sheet, or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). In various embodiments, the radiographic marker could be a spherical shape or a ring around the depot.

In one exemplary embodiment, a drug depot for delivering a therapeutic agent to a target tissue site beneath the skin of a patient is provided, the drug depot comprising an effective amount of ketorolac, wherein the target tissue site comprises at least one muscle, ligament, tendon, cartilage, spinal disc, spinal foraminal space near the spinal nerve root, facet or synovial joint, or spinal canal.

In various embodiments, the drug depot comprises a gel, which includes a substance having a gelatinous, jelly-like, or colloidal properties at room temperature. The gel, in various embodiments, may have the ketorolac and optionally one or more additional therapeutic agents dispersed throughout it or suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

When the drug depot is a gel, in contrast to a sprayable gel that typically employs a low viscosity polymer, a gel with a higher viscosity may be desirable for other applications, for example, a gel having a putty-like consistency may be more preferable for bone regeneration applications.

In another exemplary embodiment, the gel is in viscous form is loaded with one or more drug depots (e.g., microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue. In yet another exemplary embodiment, the gel is injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, where after the gel is applied to the target site, it hardens and the drug can be released as the bodily fluid contacts the gel.

In various embodiments, the drug depot is loaded with ketorolac and optionally one or more additional therapeutic agents, and delivered to the desired target tissue site (e.g., surgical wound site, inflamed tissue, degenerative tissue, etc.) and, in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., microspheres) to begin releasing the therapeutic agent. The microspheres do not begin releasing the agent until they are released from the drug depot. So, the microspheres may be formed from an insoluble or inert substances, but soluble or active once it comes into contact with the target tissue site. Likewise, the drug depot may comprise a substance that dissolves or disperses within the tissue. As the drug depot begins to dissolve within hours to days, the drug depots (e.g., microspheres) are exposed to body fluids and begin releasing their contents. The drug depot can be formulated to optimize exposure time of the drug depot and release of the therapeutic agent from the drug depot.

In various embodiments, the drug depot (e.g., gel) is flowable and can be injected, sprayed, instilled, and/or dispensed to, on or in the target tissue site. "Flowable" means that the gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in an osteolytic lesion.

In various embodiments, the drug depot comprises poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pregelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-coglycolide), PLA-PLGA, poloxamer 407, PEG-PLGA-PEG triblock copolymers, SAIB (sucrose acetate isobutyrate) or Poly(glycolide-ϵ-caprolactone) or combinations thereof. These one or more components allow the therapeutic agent to be released from the drug depot in a controlled and/or sustained manner. For example, the drug depot containing the therapeutic agent and a polymer matrix can be injected at the target tissue site and the polymer matrix breaks down over time (e.g., hours, days) within the target tissue site releasing ketorolac and optionally additional therapeutic agents. Thus the administration of the drug depot can be localized and occur over a period of time (e.g., at least one day to about 2, 3, 4, 5, 6, 7, 8, 9, or 10 days).

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of drug depot, or a matrix or component thereof, or as the result of metabolic transformation or dissolution of the therapeutic agent(s) or conjugates of therapeutic agent(s).

In various embodiments, the drug depot can be designed to cause an initial burst dose of therapeutic agent within the first 24 hours after implantation. "Initial burst" or "burst effect" or "bolus dose" refers to the release of therapeutic agent from the drug depot during the first 24 hours after the drug depot comes in contact with an aqueous fluid (e.g., synovial fluid, cerebral spinal fluid, etc.). In various embodiments, the drug depot is designed to avoid this initial burst effect. In various embodiments, a bolus dose of a therapeutically effective amount of ketorolac will release within minutes or hours after the drug depot is implanted or injected so that pain is controlled for at least a short period of time after drug delivery.

In various embodiments, the drug depot contains one or more different release layer(s) that releases a bolus dose of ketorolac or pharmaceutically acceptable salt thereof (e.g., 0.5 mg to 60 mg at a target site beneath the skin) and one or more sustain release layer(s) that releases an effective amount of ketorolac or pharmaceutically acceptable salt thereof over a period of 3 to 10 days. In various embodiments, the one or more immediate release layer(s) comprise PLGA, which degrades faster and than the one or more sustain release layer(s), which comprises PLA, which degrades at a slower rate than the PLGA.

In various embodiments, when the drug depot comprises a gel, the gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise material to enhance viscosity and control the release of the drug such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises from about 2.5% to 60% by weight ketorolac, which is sprayed with from about 40% to 60% by weight PLGA, 5% to 40% by weight of PEG550.

The drug depot release profile can also be controlled, among other things, by controlling the particle size distribution of the components of the drug depot. In various embodiments, the particle size distribution of the components of the drug depot (e.g., ketorolac, gel, etc.) may be in the range of from about 10 μM to 100 μM so that the drug depot can easily be delivered to or at or near the target site by injection, spraying, instilling, etc. In various embodiments, the ketorolac particle size is from about 5 to 30 micrometers, however, in various embodiments ranges from about 1 micron to 250 microns may be used.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the drug depot, microspheres may be dispersed within the drug depot, the microspheres loaded with the therapeutic agent. In one embodiment, the microspheres provide for a sustained release of the therapeutic agent. In yet another embodiment, the drug depot, which is biodegradable, prevents the microspheres from releasing the therapeutic agent; the microspheres thus do not release the therapeutic agent until they have been released from the depot. For example, a drug depot may be deployed around a target tissue site (e.g., a nerve root). Dispersed within the drug depot are a plurality of microspheres that encapsulate the desired therapeutic agent. Certain of these microspheres degrade once released from the drug depot, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site.

Cannula or Needle

It will be appreciated by those with skill in the art that the depot can be administered to the target site using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot (e.g., ribbon-like fibers). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering ketorolac into a target tissue site of a patient is provided, the method comprising inserting a cannula at or near a target tissue site and implanting the drug depot containing the ketorolac at the target site beneath the skin of the patient. In various embodiments, to administer the drug depot to the desired site, first the cannula or needle can be inserted through the skin and soft tissue down to the target tissue site and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In various embodiments, the drug depot can be sutured to the target site or alternatively the drug depot can be implanted, without suturing. For example, in various embodiments, the drug depot can be a ribbon shaped depot and placed at the target site, before, during or after surgery.

In various embodiments, when the target tissue site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of one or more effective dosages of ketorolac may be used to prevent, treat or relieve the symptoms of post-operative pain and/or inflammation incidental to surgery.

"Localized" delivery includes, delivery where one or more drugs are deposited within, at or near a tissue. For example, localized delivery includes delivery to a nerve root of the nervous system or a region of the brain, or in close proximity (within about 10 cm, or preferably within about 5 cm, for example) thereto. "Targeted delivery system" provides delivery of one or more drugs depots (e.g., gels or depot dispersed in the gel, etc.) having a quantity of therapeutic agent that can be deposited at or near the target tissue site as needed for treatment of pain and/or inflammation incidental to surgery.

FIG. 1 illustrates a number of common locations within a patient that may be sites at which surgery took place. It will be recognized that the locations illustrated in FIG. 1 are merely exemplary of the many different locations within a patient that may be at which surgery took place. For example, surgery may be required at a patient's knees 21, hips 22, fingers 23, thumbs 24, neck 25, and spine 26. Thus, during or following these surgeries, the patient may experience postoperative pain and/or inflammation.

The term "pain" includes nociception and the sensation of pain, both of which can be assessed objectively and subjectively, using pain scores and other methods well-known in the art. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art.

Exemplary types of pain reducible, preventable or treatable by the methods and compositions disclosed herein include, without limitation, include post operative pain, for example, from the back in the lumbar regions (lower back pain) or cervical region (neck pain), leg pain, radicular pain (experienced in the lower back and leg from lumber surgery in the neck and arm from cervical surgery), or abdominal pain from abdominal surgery, and neuropathic pain of the arm, neck, back, lower back, leg, and related pain distributions resulting from disk or spine surgery. Neuropathic pain may include pain arising from surgery to the nerve root, dorsal root ganglion, or peripheral nerve.

In various embodiments, the pain results from "post-surgical pain" or "postoperative pain" or "surgery-induced pain", which are used herein interchangeably, and refer to pain arising in the recovery period of seconds, minutes, hours, days or weeks following a surgical procedure (e.g., hernia repair, hip surgery, abdominal surgery, orthopedic or spine surgery, etc.). Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery or a combination thereof. Target tissue site includes one or more sites beneath the skin that the drug depot can be delivered. The drug depot can be used to treat one or more target tissue sites that are involved in conditions/diseases, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, a surgical wound site or an incision site or the like.

The term "pain management medication" includes one or more therapeutic agents that are administered to reduce, prevent, alleviate or remove pain entirely. These include anti-inflammatory agents, muscle relaxants, analgesics, anesthetics, narcotics, etc., or combinations thereof.

In various embodiments, the post-surgical pain or postoperative pain or surgery-induced pain, is accompanied by inflammation. Inflammation can be an acute response to trauma or surgery. When tissues are damaged, TNF-α attaches to cells to cause them to release other cytokines that cause inflammation. The purpose of the inflammatory cascade is to promote healing of the damaged tissue, but once the tissue is healed the inflammatory process does not necessarily end. Left unchecked, this can lead to degradation of surrounding tissues and associated pain. Thus, pain can become a disease state in itself. That is, when this pathway is activated, inflammation and pain ensue. Often a vicious and seemingly endless cycle of insult, inflammation, and pain sets in.

Figure 2:
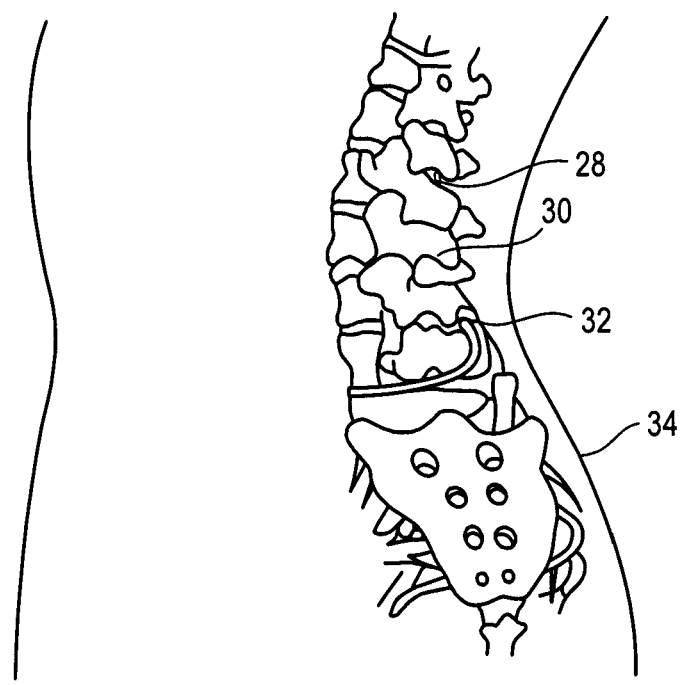
FIG. 2 illustrates a schematic dorsal view of the spine and sites where a drug depot containing ketorolac can locally be administered thereto.

One exemplary embodiment where the depot is suitable for use in pain and/or inflammation management (e.g., post operative pain and/or inflammation management) is illustrated in FIG. 2. Schematically shown in FIG. 2 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. In various embodiments, the drug depot containing ketorolac can be administered to the patient intra-operatively, intravenously, intramuscularly, SC, intrathecally, intradiscally, peridiscally, epidurally, perispinally, or parenterally or combinations thereof.

The term "patient" refers to organisms from the taxonomy class "mammalian," including but not limited to humans, other primates such as chimpanzees, apes orangutans and monkeys, rats, mice, cats, dogs, cows, horses, etc.

Method of Making Ketorolac Depots

In various embodiments, the drug depot comprising the ketorolac can be made by combining a biocompatible, biodegradable polymer and a therapeutically effective amount of ketorolac or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: ketorolac and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: ketorolac, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, ketorolac tromethamine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the ketorolac containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., ketorolac tromethamine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of ketorolac tromethamine, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where a water-soluble therapeutic agent such as ketorolac tromethamine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, ketorolac tromethamine is used and mixed or sprayed with the PLGA or PEG550 polymer, and the resulting depot may be formed by extrusion and dried.

Having now generally described the invention, the same may be more readily understood through the following reference to the following examples, which are provided by way of illustration and are not intended to limit the present invention unless specified.

Example 1

Often times when the polymer is a heteropolymer or copolymer, there is a mixture of monomer species in the polymer. The mole ratio may be indicated and varied from 0:100 to 100:0 and ranges in between these mole ratios. For example, 50:50 PLGA, the 50 refers to the monomer mole % 50 of DL (poly DL-lactide) in the polymer, while the 50 refers to the mole percent of the PGA (polyglycolide) in the polymer.

The second number, which follows the letter code for the polymer, is the target IV designator and is 10 times the midpoint of a range in dl/g. In various embodiments, the inherent viscosity ranges from 0.05-0.15, or 0.05 to 1.0. The polymer may have an ester or an acidic (indicated by the A) end group.

Materials:

Poly (d,l lactide-co-glycolide) having a 50:50 lactide to glycolide molar ratio (PLGA50501A), an intrinsic viscosity of 0.12 and acid end capped polymer chain ends was purchased from Lakeshore Biomaterials (Birmingham, Ala.). Ketorolac Tromethamine was purchased from Spectrum Chemicals (Gardena, Calif.). Methoxy-polyethylene glycol 550 (mPEG 550) was purchased from Sigma-Aldrich.

Methods:

Preparation of Spray Dried Ketorolac Tromethamine

Ketorolac tromethamine was dissolved in methanol to yield a 10% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 20° C. and 15 mmHg vacuum.

Preparation of Spray Dried Ketorolac Tromethamine/ PLGA50501A

Ketorolac tromethamine and PLGA50501A were both dissolved in acetone to yield a 2% (w/w) solution. A mixture of 10% Ketorolac tromethamine solution and 90% PLGA50501A solution was spray dried in the Buchi Spray Dryer. The processing parameters were set as follows: inlet temp. (60° C.), aspirator (80%), nitrogen inlet (50 mm), spray flow rate (80 mL/hr) and ultrasonic generator (0.8 watts). The spray dried powder was collected and dried for additional 24 hours at 20° C. and 15 mmHg vacuum.

Preparation of Melt Extruded Rods

The formulation contained PLGA8515 ground into powder using a Retsch (Retsch GmbH, Germany) rotor mill with an 80 micrometer sieve filter and Ketorolac tromethamine used as received from the manufacturer. The formulation contained 60% (w/w) ketorolac tromethamine, 10% (w/w) mPEG 550 and 30% (w/w) PLGA50501A. The formulation were dry mixed with a spatula prior to being feed into a Haake Mini-Lab twin screw extruder (Thermo Fischer Scientific, Waltham, Mass.) set at 85° C. and 30 RPM. The rods were extruded out of a 1.5 mm diameter die. After extrusion, the rods were placed in a Carver heat press at 50° C. and gently pressed to a film thickness of 1 mm.

Example 2

In-Vitro Drug Elution Testing

The formulations were cut with a razor blade to lengths of 9 mm length by 3 mm width and 1 mm thickness. Samples were placed in 20 mL scintillation vials for drug elution testing. The sample were incubated in 10 mL of phosphate buffered saline pH 7.4 (Hyclone, 0.0067M) at 37° C. under mild agitation. At pre-selected times, the buffer was removed for analysis and replaced with fresh buffer medium. The drug content was quantified at 250 nm by Molecular Devices SpectraMax M2 (Sunnyvale, Calif.) plate reader.

Example 3

Ketorolac depot formulations were prepared with drug load, polymers and excipients as listed in Table 1. The drug loads were 30 wt % to 60 wt % and 50:50 DLG (poly(DL-lactide-co-glycolide) polymer or POE (polyorthoester polymer). Excipients were used with DLG and included mPEG at 5 wt % and 10 wt %.

TABLE 1

| | Ketorolac Formulation ID | Polymer | Drug Load (%) | Excipient | Ribbon Size (mm) (L × W × H) | Processing |
|---|---|---|---|---|---|---|
| Ribbons | 13335-76-7 | 5050 DLG 1A | 60 | 10% mPEG | 9 × 3 × 1 | Melt extrusion, heat press |
| | 13335-83-7 | 5050DLG 1A | 60 | 5% mPEG | 9 × 3 × 1 | Melt extrusion, heat press |

| | Formulation ID | Polymer (Notebook ID) | Drug Load (%) | Excipients | Chemistry | Processing |
|---|---|---|---|---|---|---|
| POE Gels | 13160-54-1 | POE12 | 30 | | TEG:DET:DEGMEE 16.4:10.9.72.7 | Speed Mix |

Figure 3:
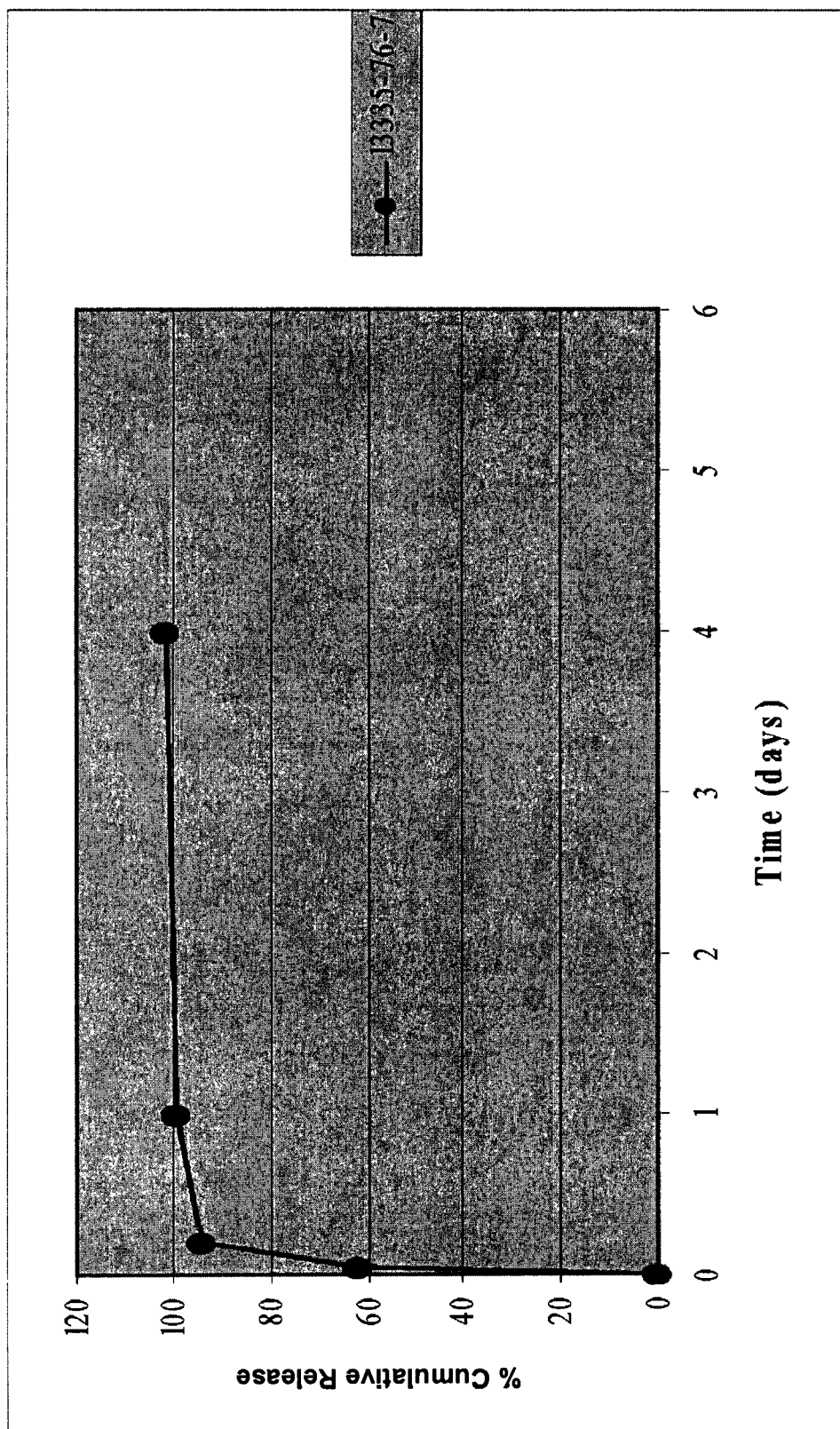
FIGS. 3-5 show ketorolac release from various formulations listed in Table 1. These formulations had bolus release, which will be effective to treat, among other things, postoperative pain.
Figure 4:
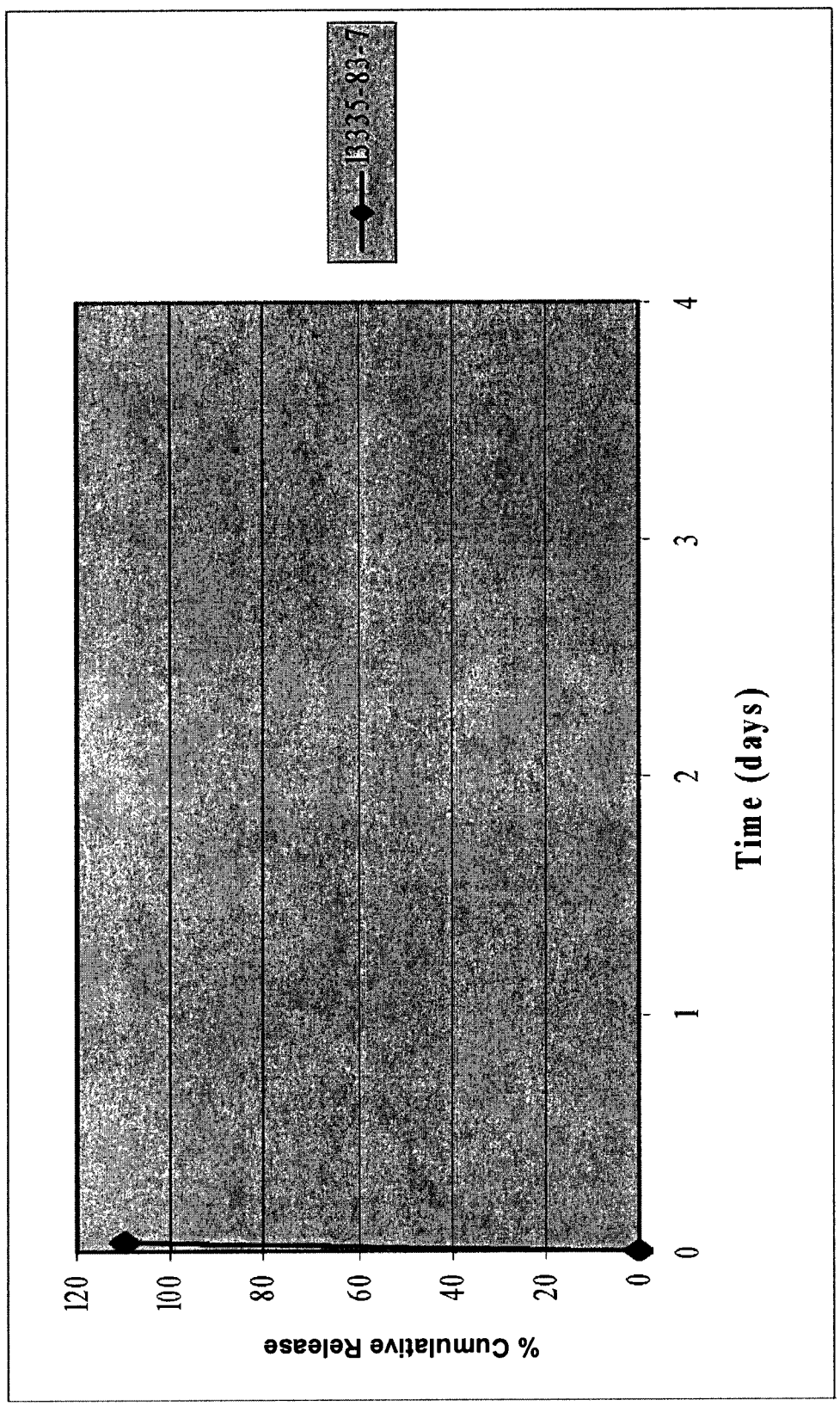
Figure 5:
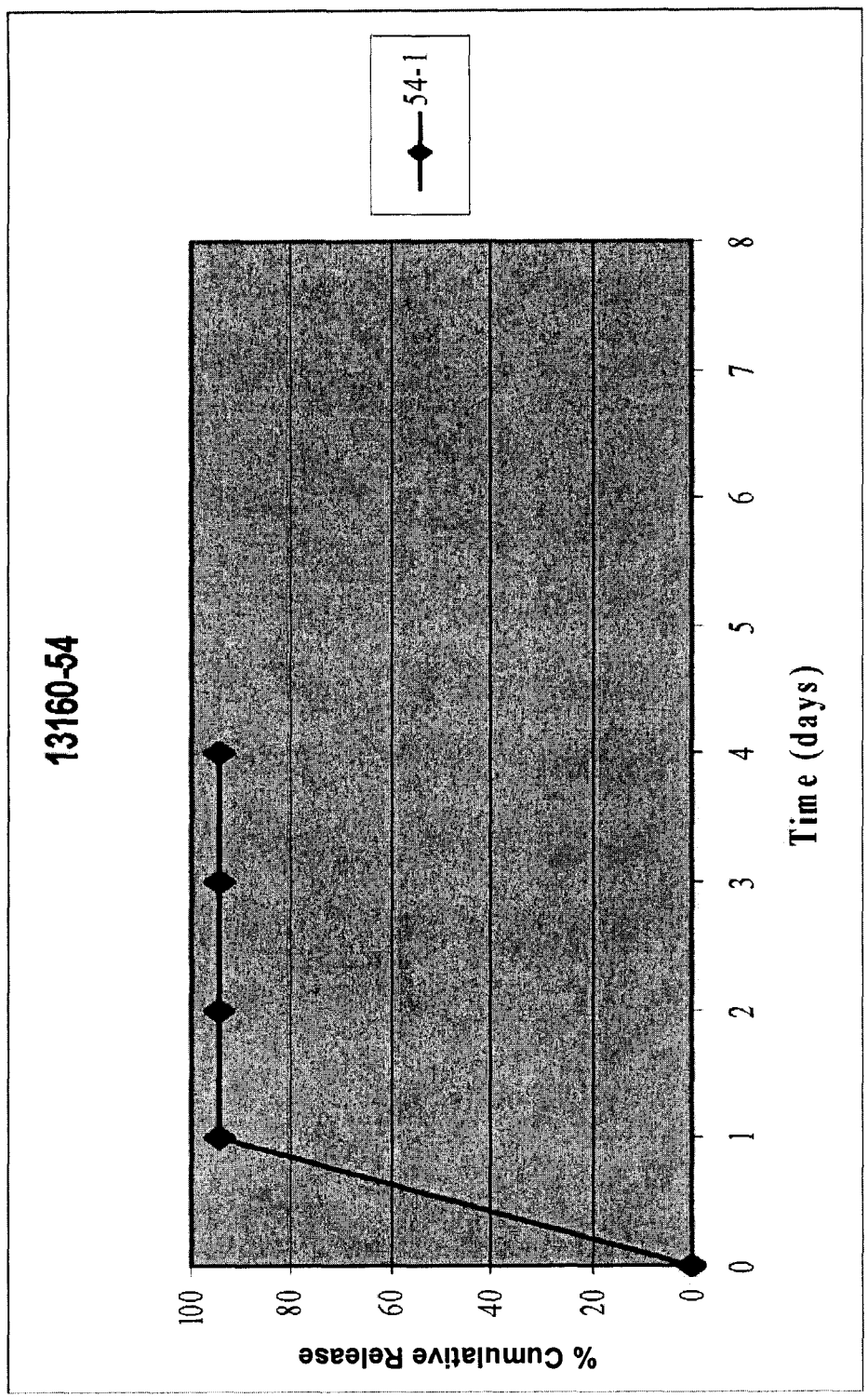

The cumulative release rates for the various formulations in Table 1 are shown in FIGS. 3-5 and may be used to design formulations that have an initial burst or bolus release if that release profile is desired. FIG. 3 illustrates the release profile for the formulation containing a 60 wt % ketorolac drug load in the depot, 10% mPEG and remainder 5050 DLG.

The codes within the table for the polymer are explained as follows. The first number or numbers refers to monomer mole percentage ratio of DL-lactide (e.g., polylactide) to glycolide (e.g., poly-glycolide). The letter code that follows the first number refers to the polymer(s) and is the polymer identifier. The second number, which follows the letter code for the polymer, is the target IV designator and is 10 times the midpoint of a range in dl/g. The meanings of certain IV designators is reflected in Table A below.

TABLE A

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |

The final letter within the code of the polymer is the end group designator. For examples "E" refers to an ester end group, while "A" refers to an acid end group.

The polymers may have different end groups such as acid and ester end groups. Implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl, and/or ethyl ester end groups).

By way of example, 100 DLG 1A is a polymer that has an inherent viscosity of 0.05-0.150 dL/g. It contains 100% DLG that has acidic end groups. It is available from Lakeshore Biomaterials, Birmingham, Ala.

FIG. 3 illustrates the release profile for the formulation containing a 60 wt % ketorolac drug load in the depot, 10 wt % mPEG and remainder 5050 DLG. The drug depot releases most of its ketorolac within 1 day and would be good for an initial burst effect. 100% of the ketorolac was released within 4 days from the drug depot.

FIG. 4 illustrates the release profile for the formulation containing a 60 wt % ketorolac drug load in the depot, 5 wt % mPEG and remainder 5050 DLG. The drug depot releases 100% of its ketorolac within a few hours and would be good for an initial burst effect. The lower % of mPEG had increased the release profile.

FIG. 5 illustrates the release profile for the formulation containing a 30 wt % ketorolac drug load in the depot, with remainder POE. The drug depot releases about 90% of its ketorolac within a few hours and would be good for an initial burst effect. About 100% of the ketorolac was released within 4 days from the drug depot.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for reducing or treating postoperative pain or inflammation in a patient in need of such treatment, the implantable drug depot comprising a therapeutically effective amount of ketorolac or pharmaceutically acceptable salt thereof, the depot being implantable at a site beneath the skin to reduce or treat postoperative pain, wherein the drug depot releases 0.5 mg to 60 mg of ketorolac or pharmaceutically acceptable salt thereof over 24 hours and wherein the drug depot comprises a biodegradable polymer having an inherent viscosity of about 0.05 to about 0.15 dL/g and the drug depot releases 25%, 30%, 40%, 50%, 60, 70%, 80%, 90%, 95%, or 99% of the ketorolac or pharmaceutically acceptable salt thereof relative to a total amount of ketorolac loaded in the drug depot over a period of 3 to 10 days after the drug depot is administered to the target tissue site and the drug depot comprises from about 5% to about 30% by weight of mPEG, and the biodegradable polymer comprises poly(lactide-co-glycolide) (PLGA) or polylactide (PLA).

2. A method of treating postoperative pain or inflammation in a patient in need of such treatment, the method comprising administering one or more biodegradable drug depots comprising a therapeutically effective amount of ketorolac or pharmaceutically acceptable salt thereof to a target tissue site beneath the skin, wherein the drug depot releases 0.5 mg to 60 mg of ketorolac or pharmaceutically acceptable salt thereof over 24 hours and wherein the drug depot comprises a biodegradable polymer having an inherent viscosity of about 0.05 to about 0.15 dL/g and the drug depot releases 25%, 30%, 40%, 50%, 60%, 70%, 80%, 90%, 95%, or 99% of the ketorolac or pharmaceutically acceptable salt thereof relative to a total amount of ketorolac loaded in the drug depot over a period of 3 to 10 days after the drug depot is administered to the target tissue site and the drug depot comprises from about 5% to about 30% by weight of mPEG, and the biodegradable polymer comprises poly (lactide-co-glycolide) (PLGA) or polylactide (PLA).

3. A method of treating postoperative pain or inflammation according to claim 2, wherein one or more drug depots release an effective amount of ketorolac or pharmaceutically acceptable salt thereof over a period of 5 to 7 days.

4. A method of treating postoperative pain or inflammation according to claim 2, wherein the ketorolac comprises ketorolac tromethamine.

5. A method of treating postoperative pain or inflammation according to claim 2, wherein the target tissue site comprises at least one muscle, ligament, tendon, cartilage, spinal disc, spinal foraminal space near the spinal nerve root, facet or synovial joint, or spinal canal.

6. A method of treating postoperative pain or inflammation according to claim 2, wherein the drug depot comprises at least one additional anti-inflammatory or analgesic agent, at least one anabolic or an anti-catabolic growth factor or a combination thereof.

7. A method of treating postoperative pain or inflammation according to claim 2, wherein the ketorolac or pharmaceutically acceptable salt thereof is encapsulated in a plurality of depots comprising microparticles, microspheres, microcapsules, and/or micro fibers.

8. A method of treating postoperative pain or inflammation according to claim 2, wherein the pain or inflammation is associated with hernia repair, orthopedic or spine surgery or a combination thereof.

9. A method of treating postoperative pain or inflammation according to claim 8, wherein the surgery is arthroscopic surgery, an excision of a mass, spinal fusion, thoracic, cervical, or lumbar surgery, pelvic surgery or a combination thereof.

10. A method of treating postoperative pain or inflammation according to claim 2, wherein the drug depot comprises a radiographic marker adapted to assist in radiographic imaging.

11. A method of treating postoperative pain or inflammation according to claim 10, wherein the radiographic marker comprises barium, calcium, or a combination thereof.

12. A method of reducing postoperative pain or inflammation in a patient in need of such treatment, the method comprising delivering one or more biodegradable drug depots comprising a therapeutically effective amount of ketorolac or pharmaceutically acceptable salt thereof to a target tissue site beneath the skin before, during or after surgery, wherein the drug depot releases 0.5 mg to 60 mg of ketorolac or pharmaceutically acceptable salt thereof over 24 hours and wherein the drug depot comprises a biodegradable polymer having an inherent viscosity of about 0.05 to about 0.15 dL/g and the drug depot releases 25%, 30%, 40%, 50%, 60%, 70%, 80%, 90%, 95%, or 99% of the ketorolac or pharmaceutically acceptable salt thereof relative to a total amount of ketorolac loaded in the drug depot over a period of 3 to 10 days after the drug depot is administered to the target tissue site and the drug depot comprises from about 5% to about 30% by weight of mPEG and the biodegradable polymer comprises poly (lactide-co-glycolide) (PLGA) or polylactide (PLA).

13. A method of reducing postoperative pain or inflammation according to claim 12, wherein one or more drug depots release an effective amount of ketorolac or pharmaceutically acceptable salt thereof over a period of 5 to 7 days.

14. A method of reducing postoperative pain or inflammation according to claim 12, wherein the ketorolac comprises ketorolac tromethamine.

15. A method of reducing postoperative pain or inflammation according to claim 12, wherein the drug depot comprises at least one additional anti-inflammatory or analgesic agent, at least one anabolic or an anti-catabolic growth factor or combination thereof.

* * * * *